United States Patent [19]

Krüger et al.

[11] Patent Number: 4,575,517

[45] Date of Patent: Mar. 11, 1986

[54] MICROBICIDAL AGENT FOR PRESERVING INDUSTRIAL MATERIALS

[75] Inventors: Bernd-Wieland Krüger, Wuppertal; Uwe Priesnitz, Solingen; Gerhard Jäger, Leverkusen; Wilfried Paulus; Hermann Genth, both of Krefeld, all of Fed. Rep. of Germany

[73] Assignee: Bayer Aktiengesellschaft, Leverkusen, Fed. Rep. of Germany

[21] Appl. No.: 580,902

[22] Filed: Feb. 16, 1984

[30] Foreign Application Priority Data

Feb. 19, 1983 [DE] Fed. Rep. of Germany ....... 3305834

[51] Int. Cl.$^4$ ..................... A01N 31/04; A01N 33/04; A01N 43/653; A01N 43/00
[52] U.S. Cl. .................................. 514/715; 514/385; 514/399; 514/383; 514/713; 514/717; 514/719; 514/646; 514/759; 427/384; 568/669; 568/661; 568/39; 560/124; 564/454; 564/455; 252/384
[58] Field of Search ................ 568/669, 661; 560/124; 514/383, 385, 399, 713, 715, 719, 717, 646, 759

[56] References Cited

U.S. PATENT DOCUMENTS 3,047,633 7/1962 Brusson et al. ..................... 568/669
3,636,161 1/1972 Robinson .
4,012,430 3/1977 Verbrugge et al. ................ 560/124

FOREIGN PATENT DOCUMENTS 2942618 4/1980 Fed. Rep. of Germany .

OTHER PUBLICATIONS

Elliott et al., Chemical Society Reviews, vol. 7, No. 4 (1978), 473–485.

Primary Examiner—Bernard Helfin
Attorney, Agent, or Firm—Sprung Horn Kramer & Woods

[57] ABSTRACT

Cyclopropylmethyl(ene) ethers have an outstanding action in microbicidal agents for preserving industrial materials from damage or destruction by microorganisms.

28 Claims, No Drawings

MICROBICIDAL AGENT FOR PRESERVING INDUSTRIAL MATERIALS

The invention relates to microbicidal agents for preserving industrial materials from damage or destruction by microorganisms.

A microbicidal agent for preserving industrial materials has been found which contains cyclopropylmethyl(ene) ethers of the formula

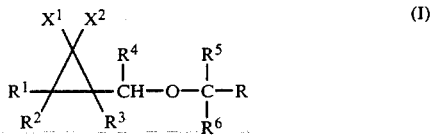

in which $X^1$ and $X^2$ are identical or different and represent halogen, $R^1$ represents hydrogen or alkyl, $R^2$ and $R^3$ are identical or different and represent hydrogen, alkyl, optionally substituted aryl, halogenoalkyl, hetaryl-alkyl, alkoxyalkyl, alkylthioalkyl, optionally substituted alkenoxyalkyl, optionally substituted alkinoxyalkyl or (di)alkylaminoalkyl, $R^4$ represents hydrogen or alkyl, $R^5$ and $R^6$ are identical or different and represent hydrogen or optionally substituted radicals from the series comprising alkyl, aryl and aralkyl and R represents a trihalogenoalkenyl, alkinyl or iodoalkinyl radical.

The microbicidal agents according to the invention have an outstanding action for preserving industrial materials from damage or destruction by microorganisms.

Alkyl $R^1$, $R^2$, $R^3$ or $R^4$ and optionally substituted alkyl $R^5$ or $R^6$ can be straight-chain or branched alkyl with 1 to 20, preferably 1 to 10, particularly preferably 1 to 6 and especially preferably 1 to 4, carbon atoms. Examples which may be mentioned are optionally substituted methyl, ethyl, n- and iso-propyl and n-, iso-, sec.- and tert.-butyl.

Iodoalkinyl R and alkinyl R preferably contain 2 to 5, in particular 2 to 4, carbon atoms in the alkinyl part. Examples which may be mentioned are ethinyl, prop-1-inyl, prop-2-inyl and but-3-inyl and the corresponding iodine derivatives.

Optionally substituted aryl $R^2$, $R^3$, $R^5$ or $R^6$ is aryl with preferably 6 or 10 carbon atoms in the aryl part. Examples which may be mentioned are optionally substituted phenyl and naphthyl, in particular phenyl.

Optionally substituted aralkyl $R^5$ or $R^6$ is aralkyl which is optionally substituted in the aryl part and/or alkyl part and has preferably 6 or 10, in particular 6, carbon atoms in the aryl part and preferably 1 to 4, in particular 1 or 2, carbon atoms in the alkyl part, it being possible for the alkyl part to be straight-chain or branched. Examples which may be mentioned are optionally substituted benzyl and phenethyl.

Halogenoalkyl radicals $R^2$ and $R^3$ contain preferably 1 to 4 carbon atoms, in particular 1 or 2 carbon atoms, in the alkyl part and preferably 1 to 5, in particular 1 to 3, halogen atoms, the halogen atoms being identical or different and preferred halogen atoms being chlorine or bromine. Examples which may be mentioned are chloromethyl and bromomethyl.

Alkoxyalkyl and alkylthioalkyl radicals $R^2$ and $R^3$ contain preferably 1 to 4 carbon atoms, in particular 1 or 2 carbon atoms, in each alkyl part, it being possible for the alkyl part to be straight-chain or branched. Examples which may be mentioned are methoxymethyl, methoxyethyl, ethoxymethyl, ethoxyethyl, methylthiomethyl, methylthioethyl, ethylthiomethyl and ethylthioethyl.

Optionally substituted alkenoxyalkyl $R^2$ or $R^3$ is alkenoxyalkyl which is optionally substituted in the alkenoxy part and/or alkyl part and has preferably 2 to 5, in particular 2 to 4, carbon atoms in the alkenoxy part and preferably 1 to 4, in particular 1 or 2, carbon atoms in the alkyl part, it being possible for the alkyl part to be straight-chain or branched. Examples which may be mentioned are optionally substituted propenyloxymethyl, butenyloxymethyl and methyl-propenyloxymethyl.

Optionally substituted alkinoxyalkyl $R^2$ or $R^3$ is alkinoxyalkyl which is optionally substituted in the alkinoxy part and/or alkyl part and has preferably 2 to 5, in particular 2 to 4, carbon atoms in the alkinoxy part and preferably 1 to 4, in particular 1 or 2, carbon atoms in the alkyl part, it being possible for the alkyl part to be straight-chain or branched. Examples which may be mentioned are optionally substituted propinyloxymethyl, butinyloxymethyl and methylpropinyloxy.

(Di)alkylamino-alkyl radicals $R^2$ and $R^3$ preferably contain 1 to 4 carbon atoms, in particular 1 or 2 carbon atoms, in the alkyl part. Examples which may be mentioned are (di)methylamino-methyl, (di)methylamino-ethyl, (di)ethylamino-methyl and (di)ethylamino-ethyl. (Di)alkylamino-alkyl denotes mono- or di-alkylamino-alkyl.

Hetaryl-alkyl radicals $R^2$ and $R^3$ contain, in the hetaryl part, 5-membered to 7-membered, preferably 5-membered or 6-membered, rings with preferably 1 to 3, in particular 1 or 2, identical or different heteroatoms such as oxygen, sulphur and/or nitrogen, preferably nitrogen, and 1 to 4 carbon atoms, in particular 1 or 2 carbon atoms, in the alkyl part. Examples which may be mentioned are 1-pyrazolylmethyl, 1-imidazolylmethyl and 1-(1,2,4-triazolyl)-methyl.

Halogen denotes fluorine, chlorine, bromine or iodine, preferably fluorine, chlorine or bromine and particularly preferably chlorine or bromine.

Trihalogenoalkenyl R contains, in the alkenyl part, straight-chain or branched alkenyl with preferably 2 to 5, in particular 2 to 4, carbon atoms. The halogen atoms can be identical or different and preferably represent fluorine, chlorine, bromine and/or iodine, in particular chlorine, bromine and/or iodine. Examples which may be mentioned are triiodoethenyl, dibromo-iodoethenyl and dichloro-iodoethenyl.

The substituted radicals mentioned in the definitions of $R^2$, $R^3$, $R^5$ and $R^6$ can carry one or more, preferably 1 to 3 and in particular 1 or 2, identical or different substituents. Examples of substituents which may be mentioned are: alkyl with preferably 1 to 4, in particular 1 or 2, carbon atoms, such as methyl, ethyl and n- and iso-propyl; alkoxy with preferably 1 to 4, in particular 1 or 2, carbon atoms, such as methoxy, ethoxy and n- and iso-propoxy; alkylthio with preferably 1 to 4, in particular 1 or 2, carbon atoms, such as methylthio, ethylthio and n- and iso-propylthio; halogen, preferably fluorine, chlorine, bromine and iodine, in particular chlorine, bromine and iodine; cyano and nitro; and halogenoalkyl, halogenoalkoxy and halogenoalkylthio with preferably 1 to 4, in particular 1 or 2, carbon atoms and 1 to 5, in particular 1 to 3, halogen atoms, such as trifluoromethyl, trifluoromethoxy and trifluoromethylthio.

Preferred microbicidal agents according to the invention contain cyclopropylmethyl(ene) ethers of the formula

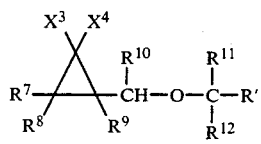 (II)

in which
X$^3$ and X$^4$ are identical or different and represent fluorine, chlorine and/or bromine,
R$^7$ represents hydrogen or C$_1$–C$_6$-alkyl,
R$^8$ and R$^9$ are identical or different and represent hydrogen, C$_1$–C$_6$-alkyl, C$_1$–C$_4$-halogenoalkyl, 1-pyrazolylmethyl, 1-imidazolylmethyl, 1-(1,2,4-triazolyl)-methyl, C$_1$–C$_4$-alkoxy-C$_1$–C$_4$-alkyl, C$_1$–C$_4$-alkylthio-C$_1$–C$_4$-alkyl, (di)C$_1$–C$_4$-alkylamino-C$_1$–C$_4$-alkyl or a radical from the series phenyl, C$_2$–C$_4$-alkenoxy-C$_1$–C$_2$-alkyl and C$_2$–C$_4$-alkinoxy-C$_1$–C$_2$-alkyl which is optionally substituted by halogen, such as, in particular, chlorine, bromine or iodine,
R$^{10}$ represents hydrogen or C$_1$–C$_4$-alkyl,
R$^{11}$ and R$^{12}$ are identical or different and represent hydrogen, C$_1$–C$_4$-alkyl or a radical from the series phenyl, benzyl and phenethyl which is optionally substituted by halogen, such as, in particular, chlorine, bromine or iodine, and R' represents triiodo-C$_2$–C$_4$-alkenyl, dibromo-iodo-C$_2$–C$_4$-alkenyl, dichloro-iodo-C$_2$–C$_4$-alkenyl, C$_2$–C$_4$-alkinyl or iodo-C$_2$–C$_4$-alkinyl.

Particularly preferred microbicidal agents according to the invention contain cyclopropylmethyl(ene) ethers of the formula

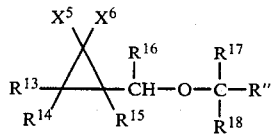 (III)

in which
X$^5$ and X$^6$ are identical or different and represent chlorine and/or bromine,
R$^{13}$ represents hydrogen, methyl, ethyl, n-propyl or n-butyl, R$^{14}$ and R$^{15}$ are identical or different and represent hydrogen, methyl, ethyl, n-propyl, n-butyl, 1-pyrazolylmethyl, 1-imidazolylmethyl, 1-(1,2,4-triazolyl)-methyl, methoxymethyl, ethoxymethyl, ethoxyethyl, methylthiomethyl, ethylthiomethyl, ethylthioethyl, (di)methylaminomethyl, (di)methylaminoethyl, (di)ethylaminomethyl, (di)ethylaminoethyl, propenyloxymethyl, propinyloxymethyl, iodopropinyloxymethyl, triiodopropenyloxymethyl, dichloro-iodopropenyloxymethyl, dibromo-iodopropenyloxymethyl, phenyl, 2-, 3-, 4-chlorophenyl, 2,4-dichlorophenyl, 2-, 3-, 4-bromophenyl, 2,4-dibromophenyl, chloromethyl and bromomethyl,
R$^{16}$ represents hydrogen, methyl, ethyl or n- or i-propyl,
R$^{17}$ and R$^{18}$ are identical or different and represent hydrogen, methyl, ethyl, n-propyl, i-propyl, 2-, 3-, 4-chlorophenyl, 2,4-dichlorophenyl or 4-bromophenyl and
R'' represents triiodoethenyl, dichloro-iodoethenyl, dibromo-iodoethenyl, iodoethinyl, or iodopropinyl.

Especially preferred microbicidal agents according to the invention contain cyclopropylmethyl(ene) ethers of the formula

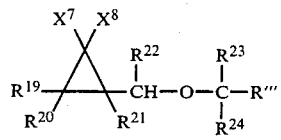 (IV)

in which
X$^7$ and X$^8$ are identical or different and represent chlorine and/or bromine,
R$^{19}$ represents hydrogen, methyl or ethyl,
R$^{20}$ and R$^{21}$ are identical or different and represent hydrogen, methyl, ethyl, chloromethyl, bromomethyl, 1-propenyloxymethyl, 1-propinyloxymethyl or 1-iodopropinyloxymethyl,
R$^{22}$ represents hydrogen or methyl,
R$^{23}$ and R$^{24}$ are identical or different and represent hydrogen or methyl and
R''' represents triiodoethenyl, dichloro-iodoethenyl, dibromo-iodoethenyl or iodoethinyl.

The cyclopropylmethyl(ene) ethers listed in the following table may be mentioned specifically:

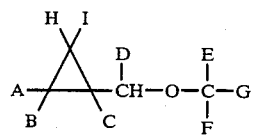

TABLE

| H | I | A | B | C | D | E | F | G |
|---|---|---|---|---|---|---|---|---|
| Cl | Cl | H | H | H | H | H | H | —C≡CH |
| Cl | Cl | H | H | H | H | H | H | —C≡CI |
| Cl | Cl | H | H | H | H | H | H | —CBr=CBrI |
| Cl | Cl | H | H | H | H | H | H | —CBr=CBrI |
| Cl | Cl | H | H | H | H | H | H | —CI=CI$_2$ |
| Br | Br | H | CH$_3$ | H | H | H | H | —C≡CH |
| Cl | Cl | H | CH$_3$ | H | H | H | H | —C≡CH |
| Br | Br | H | H | H | H | H | H | —C≡CH |
| Br | Br | H | H | H | H | H | H | —C≡CI |
| Cl | Cl | H | CH$_3$ | H | H | H | H | —C≡CI |
| Cl | Cl | H | H | CH$_3$ | H | H | H | —C≡CI | ylthio-phthalimide and N,N-dimethyl-N'-phenyl-(N'-fluorodichloromethylthio)-sulphamide, compounds which split off formaldehyde, such as hemiformals, oxazolidines, hexahydro-s-triazines, N-methylolamides and phenol derivatives, such as p-chloro-m-cresol, 2-phenylphenol and (2,2'-dihydroxy-5,5'-dichloro)-diphenylmethane.

Surprisingly, the microbicidal agents according to the invention which contain cyclopropylmethyl(ene) ethers as the active compound have a more powerful specific action than comparable agents. They are distinguished in particular by a low use concentration.

PREPARATION EXAMPLES

Example 1

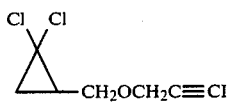

(Process a)

4.5 g (0.025 mol) of 3-(2,2-dichlorocyclopropylmethoxy)-1-propine are dissolved in 100 ml of methanol, and 6.3 g (0.025 mol) of iodine and 2.5 g of 45% strength sodium hydroxide solution are added in alternating portions at 20° C. After the addition, stirring is continued at 20° C. for 1 hour. After the methanol has been distilled off, the residue is taken up in 100 ml of methylene chloride and the mixture is washed with 50 ml of dilute sodium thiosulphate solution and then with 50 ml of water. The organic phase is dried over magnesium sulphate.

After distilling off volatile constituents under 1 mbar at 95° C., 3.8 g (50% of theory) of 3-(2,2-dichlorocyclopropylmethoxy)-1-iodo-1-propine of refractive index $n^{20}$: 1.5818 are obtained as the residue.

Example 2

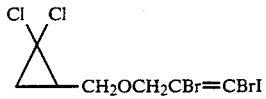

(Process b)

3 g (0.01 mol) of 3-(2,2-dichlorocyclopropylmethoxy)-1-iodo-1-propine are dissolved in 50 ml of methylene chloride, and 2 g (0.0125 mol) of bromine in 20 ml of methylene chloride are added at 20° C. The mixture is then stirred at 60° C. for 14 hours. After cooling to 20° C., the mixture is washed with 20 ml of aqueous sodium thiosulphate solution and then with water. The organic phase is dried over magnesium sulphate and the solvent is removed under a water pump vacuum.

4.2 g (90% of theory) of 1,2-dibromo-3-(2,2-dichlorocyclopropylmethoxy)-1-iodo-1-propene of refractive index $n_D^{20}$: 1.6014 are obtained.

Example 3

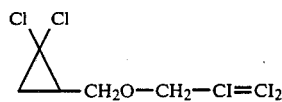

(Process a)

96 g (0.378 mol) of iodine and 13 g of 45% strength sodium hydroxide solution are added in alternating portions to 23 g (0.128 mol) of 3-(2,2-dichlorocyclopropylmethoxy)-1-propine in 100 ml of methanol at 20° C., while stirring, and the mixture is stirred for 14 hours. The solvent is then distilled off under a water pump vacuum and 500 ml of methylene chloride are added to the residue. The mixture is washed first with 200 ml of dilute sodium thiosulphate solution and then with 200 ml of water, until decoloration. The organic phase is dried over magnesium sulphate and concentrated under a water pump vacuum.

46 g (64% of theory) of 3-(2,2-dichlorocyclopropylmethoxy)-1,1,2-triiodo-1-propene of refractive index $n_D^{20}$: 1.6623 are obtained.

The compounds of the formula (I) listed in Table 1 which follows can be prepared analogously to process variant (a) or (b):

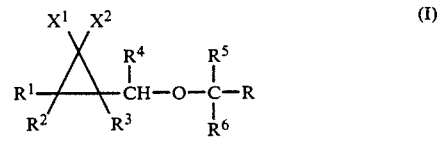

TABLE 1

| Example No. | X¹ | X² | R¹ | R² | R³ | R⁴ | R⁵ | R⁶ | R | $n_D^{20}$ |
|---|---|---|---|---|---|---|---|---|---|---|
| 4 | Br | Br | H | H | H | H | H | H | —C≡CI | 1.5980 |
| 5 | Cl | Cl | H | CH₃ | H | H | H | H | —C≡CI | 1.5540 |
| 6 | Cl | Cl | H | H | CH₃ | H | H | H | —C≡CI | 1.5530 |
| 7 | Br | Br | H | CH₃ | H | H | H | H | —C≡CI | 1.5620 |
| 8 | Cl | Cl | H | CH₃ | H | H | H | H | —C=CI<br>\|  \|<br>Cl Cl | 1.5484 |
| 9 | Br | Br | H | CH₃ | H | H | H | H | —C=CI<br>\|  \|<br>Cl Cl | 1.5780 |
| 10 | Br | Br | H | CH₃ | H | H | H | H | —CI=CI₂ | 1.6496 |
| 11 | Cl | Cl | H | CH₃ | H | H | H | H | —CBr=CBrI | 1.5920 |
| 12 | Cl | Cl | H | CH₃ | H | H | H | H | —CI=CI₂ | 1.6396 |
| 13 | Cl | Cl | H | —CH₂Br | H | H | H | H | —C≡CI | 1.5565 |
| 14 | Cl | Cl | H | —CH₂OCH₂C≡CI | H | H | H | H | —C≡CI | 1.5920 |
| 15 | Cl | Cl | H | H | CH₃ | H | H | H | —CBr=CBrI | 1.5391 |
| 16 | Cl | Cl | H | H | CH₃ | H | H | H | —CI=CI₂ | 1.6464 |

TABLE-continued

| H | I | A | B | C | D | E | F | G |
|---|---|---|---|---|---|---|---|---|
| Br | Br | H | CH$_3$ | H | H | H | H | —C≡CI |
| Cl | Cl | H | H | CH$_3$ | H | H | H | —C≡CH |
| Cl | Cl | H | CH$_3$ | H | H | H | H | —C(Cl)=C(Cl)I |
| Br | Br | H | CH$_3$ | H | H | H | H | —C(Cl)=C(Cl)I |
| Br | Br | H | CH$_3$ | H | H | H | H | —CI=CI$_2$ |
| Cl | Cl | H | CH$_3$ | H | H | H | H | —CBr=CBrI |
| Cl | Cl | H | CH$_3$ | H | H | H | H | —CI=CI$_2$ |
| Cl | Cl | H | —CH$_2$Br | H | H | H | H | —C≡CH |
| Cl | Cl | H | —CH$_2$OCH$_2$C≡CH | H | H | H | H | —C≡CH |
| Cl | Cl | H | —CH$_2$Br | H | H | H | H | —C≡CI |
| Cl | Cl | H | —CH$_2$OCH$_2$C≡CI | H | H | H | H | —C≡CI |
| Cl | Cl | H | H | H | CH$_3$ | H | H | —CBr=CBrI |
| Cl | Cl | H | H | CH$_3$ | H | H | H | —CI=CI$_2$ |
| Cl | Cl | H | H | —CH$_2$Cl | H | H | H | —C≡CH |
| Cl | Cl | H | H | CH$_3$ | H | H | H | —C(Cl)=C(Cl)I |

The cyclopropylmethyl(ene) ethers according to the invention can be prepared by (a) reacting cyclopropylmethyl(ene) halides with corresponding alcohols in the presence of bases, such as, for example, sodium hydride and, if appropriate, in the presence of a diluent and reacting the compounds prepared in this manner with equimolar or excess iodine in the presence of, for example, sodium hydroxide solution and, if appropriate, in the presence of a diluent, or (b) reacting the compounds prepared according to section (a) with halogens, such as chlorine, bromine or iodine, if appropriate in the presence of a diluent.

Industrial materials in the context of the present invention are products which do not themselves occur naturally, but are manufactured from naturally occurring or synthetic starting materials. The products to be preserved in the context of the present invention are industrial materials which can be decomposed by microorganisms, e.g. non-living materials.

Examples of industrial materials which are to be preserved from microbial change and destruction by the substances according to the invention are adhesives, sizes, paper and cardboard, textiles, leather, wood, paints, plaster, cooling lubricants and articles made of plastic which can be attacked and decomposed by microorganisms. Components of production plants, such as, for example, cooling water and cooling lubricant circulations, the ability of which to function can be impaired by microorganisms may also be mentioned in the context of materials to be preserved. The active compounds according to the invention can preferably be used for the preservation of adhesives, paper, cardboard, paint films, wood and the like.

Examples of microorganisms which can cause degradation of or a change in the industrial materials are bacteria, fungi, yeasts, algae and slime organisms.

The substances according to the invention preferably act against fungi and slime organisms; both moulds and fungi which destroy or discolour wood are affected by the fungicidal action.

Microorganisms of the following genera may be mentioned as examples: Escherichia, such as *Escherichia coli*, Pseudomonas, such as *Pseudomonas aeruginosa*, Staphylococcus, such as *Staphylococcus aureus*, Alternaria, such as *Alternaria tenuis*, Aspergillus, such as *Aspergillus niger*, Aureobasidium, such as *Aureobasidium pullulans*, Chaetomium, such as *Chaetomium globosum*, Coniophora, such as, *Coniophora cerebella*, Lentinus, such as *Lentinus tigrinus*, Penicillium, such as *Penicillium glaucum*, Polyporus, such as *Polyporus versicolor*, Sclerophoma, such as *Sclerophoma pityophila* and Trichoderma, such as *Trichoderma viride*.

Depending on their field of use, the substances according to the invention can be converted into customary formulations, such as solutions, emulsions, suspensions, powders, pastes and granules. These can be prepared in a manner which is known per se, for example by mixing the active compounds with an extender, that is to say a liquid solvent and/or solid carriers, if necessary using surface-active agents, such as emulsifiers and/or dispersing agents, it being possible, for example if extenders are used, for organic solvents optionally to be used as auxiliary solvents.

Organic solvents for the active compounds can be, for example, alcohols, such as lower alcohols, preferably ethanol or isopropanol, or benzyl alcohol, ketones, such as acetone or methyl ethyl ketone, liquid hydrocarbons, such as benzine fractions, and chlorinated hydrocarbons, such as 1,2-dichloroethane.

The microbicidal agents according to the invention in general contain 10 to 100% by weight, preferably 50 to 80% by weight, of the substituted cyclopropylmethyl(ene) ethers as the active compound.

The use concentration of the substances according to the invention depends on the type and occurrence of the microorganisms to be combatted, and on the composition of the material to be preserved. The optimum amount used can be determined by test series. In general, the use concentrations are in the range from 0.001 to 5% by weight, preferably from 0.05 to 0.5% by weight, based on the material to be protected.

The new active compounds according to the invention can also be mixed with other known active compounds. The following active compounds may be mentioned as examples: benzimidazolyl methylcarbamates, tetramethylthiuram disulphide, N-fluorodichlorometh- TABLE 1-continued

| Example No. | $X^1$ | $X^2$ | $R^1$ | $R^2$ | $R^3$ | $R^4$ | $R^5$ | $R^6$ | R | $n_D^{20}$ |
|---|---|---|---|---|---|---|---|---|---|---|
| 17 | Cl | Cl | H | H | CH$_3$ | H | H | H | $-\underset{\underset{Cl}{\vert}}{C}=\underset{\underset{Cl}{\vert}}{C}l$ | 1.5547 |

USE EXAMPLES

Example 19

Action Against Fungi

The compounds according to the invention were incorporated, in stepwise concentrations of between 1 and 5,000 mg/liter of test sample, into an agar which has been prepared from beer wort and peptone. After the agar had solidified, the agar samples thus prepared were contaminated with pure cultures of various test fungi (see Table A).

After storage at 28° C. and 60 to 70% relative atmospheric humidity for two weeks, the samples were evaluated. The smallest concentration of the substance contained in an agar sample at which no growth at all of the species used took place is given in the table as the minimum inhibitory concentration (MIC).

In this test, for example, the following compounds show a very good action: compounds according to preparation examples 1, 5, 6, 7, 11, 12, 3, 15 and 16.

TABLE A

| | Action against fungi (MIC values in mg/liter for the following species) | | | | | | | | | |
|---|---|---|---|---|---|---|---|---|---|---|
| | Alternaria tenuis | Aspergillus niger | Aureobasidium pullulans | Chaetomium globosum | Coniophora cerebella | Lentinus tigrinus | Penicillium glaucum | Polyporus versicolor | Sclerophoma pityophila | Trichoderma viride |
| (1) Cl₂-cyclopropane—CH₂OCH₂—C≡CCl | 2 | 1 | 1 | 75 | 0.1 | 2 | 15 | 1 | 2 | 10 |
| (5) Cl₂-cyclopropane(CH₃)—CH₂OCH₂—C≡CCl | 5 | 2 | 3 | 75 | 0.5 | 5 | 2 | 2 | 5 | 20 |
| (6) Cl₂-cyclopropane(CH₃)—CH₂OCH₂—C≡CCl | 35 | 5 | 5 | 100 | 0.75 | 7.5 | 2 | 2 | 5 | 20 |
| (7) Br₂-cyclopropane(CH₃)—CH₂OCH₂—C≡CCl | 5 | 5 | 5 | 50 | 0.75 | 10 | 5 | 5 | 10 | 50 |
| (11) Cl₂-cyclopropane(CH₃)—CH₂OCH₂—CBr=CBrI | 200 | 500 | 100 | 350 | 20 | 75 | 200 | 100 | 100 | 500 |
| (12) Cl₂-cyclopropane(CH₃)—CH₂OCH₂—CI=CI₂ | — | 50 | — | 50 | — | — | 50 | — | — | — |

TABLE A-continued

Action against fungi (MIC values in mg/liter for the following species)

| | Alternaria tenuis | Aspergillus niger | Aureobasidium pullulans | Chaetomium globosum | Coniphora cerebella | Lentinus tigrinus | Penicillium glaucum | Polyporus versicolor | Sclerophoma pityophila | Trichoderma viride |
|---|---|---|---|---|---|---|---|---|---|---|
| Cl₂C–C(Cl)–CH₂OCH₂–Cl=Cl₂ (3) | — | <20 | — | <20 | — | — | <20 | — | — | — |
| Cl₂C–C(Cl)(CH₃)–CH₂OCH₂–CBr=CBrI (15) | — | 100 | — | 100 | — | — | 100 | — | — | — |
| Cl₂C–C(Cl)(CH₃)–CH₂OCH₂–Cl=Cl₂ (16) | — | <20 | — | 35 | — | — | <20 | — | — | — |
| Cl₂C–C(Cl)(CH₃)–CH₂OCH₂–CCl=CCII (8) | — | <20 | — | <20 | — | — | <20 | — | — | — |

Example 20

Action Against Slime Organisms

Compounds according to the invention are used, dissolved in a little acetone, in concentrations of in each case 0.1 to 100 mg/liter in Allen's nutrient solution (Arch. Mikrobiol. 17, 34 to 53 (1952)), which contains, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam. Shortly beforehand, the nutrient solution is infected with slime organisms (about $10^6$ germs/ml) which have been isolated from the spinning water circulations used in the production of polyamide. Nutrient solutions which contain the minimum inhibitor concentration (MIC) or higher concentrations of active compound are still completely clear after culture for 3 weeks at room temperature, that is to say the marked multiplication of the microbes and formation of slime noticeable after 3 to 4 days in nutrient solutions containing no active compound are absent.

In this test, for example, the following compounds show a very good action: compounds according to the preparation examples 1, 5, 6 and 7.

TABLE B

Action against slime organisms

| Acitive compound | MIC values in mg/liter for the action on slime organisms |
|---|---|
| (1) Cl,Cl-cyclopropyl—CH$_2$OCH$_2$—C≡CI | 5–10 |
| (5) Cl,Cl-cyclopropyl(CH$_3$)—CH$_2$OCH$_2$—C≡CI | 5–10 |
| (6) Cl,Cl-cyclopropyl(CH$_3$)—CH$_2$OCH$_2$—C≡CI | 5–10 |
| (7) Br,Br-cyclopropyl(CH$_3$)—CH$_2$OCH$_2$—C≡CI | 10 |

What is claimed is:

1. A microbicidal composition for preserving industrial materials comprising a microbicidally effective amount of a cyclopropylmethyl-(ene) ether of the formula

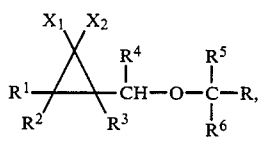

wherein
 X$^1$ and X$^2$ are identical or different and represent fluorine, chlorine and/or bromine,
 R$^1$ represents hydrogen or C$_1$–C$_6$ alkyl,
 R$^2$ and R$^3$ are identical or different and represent hydrogen, C$_1$–C$_6$ alkyl, C$_1$–C$_4$ halogenoalkyl, 1-pyrazolylmethyl, 1-imidazolylmethyl, 1-(1,2,4-triazolyl)methyl, C$_1$–C$_4$-alkoxy-C$_1$–C$_4$-alkyl, C$_1$–C$_4$-alkylthio-C$_1$–C$_4$-alkyl, (di)C$_1$–C$_4$-alkylamino-C$_1$–C$_4$-alkyl or a radical from the series phenyl, C$_2$–C$_4$-alkenoxy-C$_1$–C$_2$-alkyl and C$_2$–C$_4$-alkinoxy-C$_1$–C$_2$-alkyl which is unsubstituted or substituted by halogen:
 R$^4$ represents hydrogen or C$_1$–C$_4$-alkyl:
 R$^5$ and R$^6$ are identical or different and represent hydrogen, C$_1$–C$_4$-alkyl or a radical selected from the group consisting of phenyl, benzyl and phenethyl which is unsubstituted or substituted by halogen, and
 R represents triiodo-C$_2$–C$_4$-alkenyl, dibromo-iodo-C$_2$–C$_4$-alkinyl, dichloro-iodo-C$_2$–C$_4$-alkenyl and iodo C$_2$–C$_4$-alkinyl, in a diluent.

2. A microbicidal composition according to claim 1, wherein
 X$^1$ and X$^2$ are identical or different and represent chlorine and/or bromine,
 R$^1$ represents hydrogen, methyl, ethyl, n-propyl or n-butyl,
 R$^2$ and R$^3$ are identical or different and represent hydrogen, methyl, ethyl, n-propyl, n-butyl, 1-pyrazolylmethyl, 1-imidazolylmethyl, 1-(1,2,4-triazolyl)-methyl, methoxymethyl, ethoxymethyl, ethoxyethyl, methylthiomethyl, ethylthiomethyl, ethylthioethyl, (di)methylaminomethyl, (di)methylaminoethyl, (di)ethylaminomethyl, (di)ethylaminoethyl, propenyloxymethyl, propinyloxymethyl, iodopropinyloxymethyl, triiodopropenyloxymethyl, dichloro-iodopropenyloxymethyl, dibromo-iodopropenyloxymethyl, phenyl, 2-,3-, 4-chlorophenyl, 2,4-dichlorophenyl, 2-,3-, 4-bromophenyl, 2,4-dibromophenyl, chloromethyl and bromomethyl,
 R$^4$ represents hydrogen, methyl, ethyl or n-propyl or isopropyl,
 R$^5$ and R$^6$ are identical or different and represent hydrogen, methyl, ethyl, n-propyl, i-propyl, 2-,3-, 4-chlorophenyl, 2,4-dichlorophenyl or 4-bromophenyl, and
 R represents triiodoethenyl, dichloro-iodoethenyl, dibromo-iodoethenyl, iodoethinyl or iodopropinyl.

3. A microbicidal composition according to claim 1, wherein R$^5$ and R$^6$ are hydrogen.

4. A microbicidal composition according to claim 3, wherein R$^4$ is hydrogen.

5. A microbicidal composition according to claim 4, wherein R$^1$ is hydrogen.

6. A microbicidal composition according to claim 1, wherein R$^3$ is hydrogen.

7. A microbicidal composition according to claim 1, wherein R$^3$ is methyl.

8. A microbicidal composition according to claim 1, wherein R$^2$ is hydrogen.

9. A microbicidal composition according to claim 1, wherein R$^2$ is methyl.

10. A microbicidal composition according to claim 1, wherein R is —C≡CI.

11. A microbicidal composition according to claim 1, wherein R is —CBr═CBrI.

12. A microbicidal composition according to claim 1, wherein R is —CI═CI$_2$.

13. A microbicidal composition according to claim 1, wherein R is CCl═CCII.

14. A microbicidal composition according to claim 1, wherein $X^1$ and $X^2$ are chlorine.

15. A microbicidal composition according to claim 1, wherein $X^1$ and $X^2$ are bromine.

16. A microbicidal composition according to claim 1, wherein the ether is of the formula

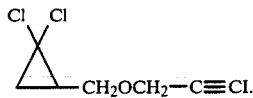

17. A microbicidal composition according to claim 1, wherein the ether is of the formula

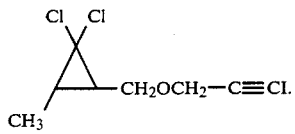

18. A microbicidal composition according to claim 1, wherein the ether is of the formula

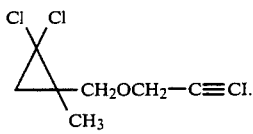

19. A microbicidal composition according to claim 1, wherein the ether is of the formula

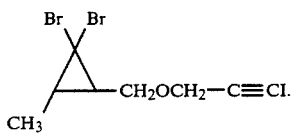

20. A microbicidal composition according to claim 1, wherein the ether is of the formula

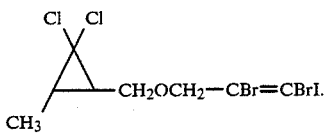

21. A microbicidal composition according to claim 1, wherein the ether is of the formula

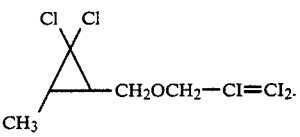

22. A microbicidal composition according to claim 1, wherein the ether is of the formula

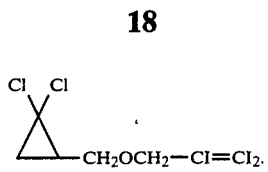

23. A microbicidal composition according to claim 1, wherein the ether is of the formula

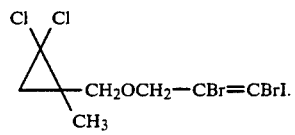

24. A microbicidal composition according to claim 1, wherein the ether is of the formula

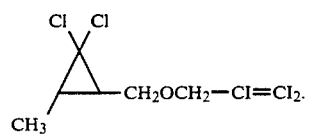

25. A microbicidal composition according to claim 1, wherein the ether is of the formula

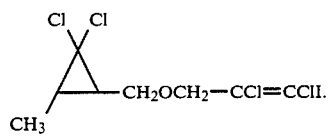

26. A composition according to claim 1, wherein said cyclopropylmethyl-(ene) ether is present in an amount of at least 10% by weight.

27. A process for rendering an industrial material less subject to attack by microorganisms which comprises applying to said industrial material a microbicidally effective amount of a cyclopropylmethyl-(ene) ether of the formula

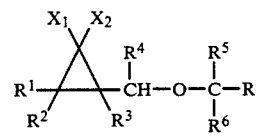

in which $X^1$ and $X^2$ are identical or different and represent fluorine, chlorine and/or bromine, $R^1$ represents hydrogen or $C_1$–$C_6$ alkyl, $R^2$ and $R^3$ are identical or different and represent hydrogen, $C_1$–$C_6$ alkyl, $C_1$–$C_4$ halogenoalkyl, 1-pyrazolylmethyl, 1-imidazolylmethyl, 1-(1,2,4-triazolyl)methyl, $C_1$–$C_4$-alkoxy-$C_1$–$C_4$-alkyl, $C_1$–$C_4$-alkylthio-$C_1$–$C_4$-alkyl, (di)$C_1$–$C_4$-alkylamino-$C_1$–$C_4$-alkyl or a radical from the series phenyl, $C_2$–$C_4$-alkenoxy-$C_1$–$C_2$-alkyl and $C_2$–$C_4$-alkinoxy-$C_1$–$C_2$-alkyl which is unsubstituted or substituted by halogen, $R^4$ represents hydrogen or $C_1$–$C_4$-alkyl;

$R^5$ and $R^6$ are identical or different and represent hydrogen, $C_1$–$C_4$-alkyl or a radical selected from the group consisting of phenyl, benzyl and phenethyl which is unsubstituted or substituted by halogen, and R represents triiodo-$C_2$–$C_4$-alkenyl, dibromo-iodo-$C_2$–$C_4$-alkinyl, dichloro-iodo-$C_2$–$C_4$-alkenyl and iodo $C_2$–$C_4$-alkinyl, in a diluent.

28. A process according to claim 27, wherein said industrial material is selected from the group consisting of adhesive, size, paper, cardboard, textiles, leather, wood, paint, building material, rubber articles, articles made of plastic and cooling lubricants.

* * * * *